United States Patent [19]

Komiya

[11] 4,245,624
[45] Jan. 20, 1981

[54] ENDOSCOPE WITH FLEXIBLE TIP CONTROL

[75] Inventor: Osamu Komiya, Hachioji, Japan

[73] Assignee: Olympus Optical Co., Ltd., Tokyo, Japan

[21] Appl. No.: 865,884

[22] Filed: Dec. 30, 1977

[30] Foreign Application Priority Data

| Jan. 20, 1977 [JP] | Japan | 52-5474 |
| Jan. 20, 1977 [JP] | Japan | 52-5475 |
| Jan. 20, 1977 [JP] | Japan | 52-5476 |

[51] Int. Cl.$^3$ ............................................. A61B 1/00
[52] U.S. Cl. .................................. 128/4; 128/349 R; 128/772; 128/DIG. 9
[58] Field of Search ........................................ 128/4-8, 128/303.15, DIG. 9, 348, 356, 772, 328, 349 R; 239/588, 602, DIG. 12, DIG. 19

[56] References Cited

U.S. PATENT DOCUMENTS

| 1,219,049 | 3/1917 | Sticklin | 239/588 |
| 1,741,740 | 12/1929 | Sederholm et al. | 128/303.15 |
| 2,129,391 | 9/1938 | Wappler | 128/6 |
| 2,753,869 | 7/1956 | Muffly | 128/348 X |
| 3,027,098 | 3/1962 | Helmer | 239/602 |
| 3,119,392 | 1/1964 | Zeiss | 128/348 X |
| 3,332,425 | 7/1967 | Luborsky et al. | 128/356 |

FOREIGN PATENT DOCUMENTS

| 2242076 | 12/1973 | Fed. Rep. of Germany | 239/602 |
| 2426781 | 12/1975 | Fed. Rep. of Germany | 128/303.15 |
| 1032414 | 7/1953 | France | 239/602 |
| 170412 | 2/1957 | Sweden | 239/588 |

*Primary Examiner*—Steven A. Bratlie

[57] ABSTRACT

An endoscope has a control section and a tube section connected to the control section to be conducted into the body cavity, wherein a channel running through the tube section contains a guide tube which is made flexible along the entire length or near the distal end portion, and reciprocates through the channel, thereby causing the distal end portion of the guide tube to be pushed out of or be withdrawn into the distal end portion of the tube section, a wire, one end of which is fixed to the distal end of the guide tube is received in the tube section so as to be pulled toward the control section, and the distal end portion of the guide tube pushed out of the distal end of the tube section can be freely flexed by the pulling force of the wire.

6 Claims, 12 Drawing Figures

ENDOSCOPE WITH FLEXIBLE TIP CONTROL

BACKGROUND OF THE INVENTION

This invention relates to an endoscope wherein improvements are made on a guide tube through which a medical implement such as forceps or a catheter is introduced into the body cavity.

Generally, the tube section of an endoscope has a channel running therethrough for introduction into the body cavity a medical implement such as forceps or a catheter. A medical implement pushed out of the distal end of the tube section is flexed or rotated to be positioned at the prescribed location within the body cavity. At said prescribed location, the medical implement picks up a sample of a coeliac tissue, sucks up water or viscous fluids such as blood and mucus held in the body cavity or washes said prescribed location.

The prior art endoscope has been so designed that an introduced medical implement is rotated together with a tube section which is made flexible at least in the near distal end portion, or the introduced medical implement is flexed or rotated by a control attachment fitted to the distal end of the tube section. However, an endoscope so constructed as to cause the near distal end portion of the tube section to be flexed has the drawbacks that not only the tube section fails to be flexed with a reduced radius of curvature, but also a large force is required for the bending of the near distal end portion of the tube section due to its high rigidity, thus preventing the tube section and medical implement introduced into the body cavity from being easily operated. On the other hand, an endoscope having a control attachment fitted to the distal end of the tube section has also the drawbacks that loading of the control attachment not only complicates the construction of the tube section, but also leads to the possibility of coeliac filth being carried between the control attachment and medical implement with the resultant unreliable operation of the control attachment and medical implement.

With both types of endoscope, an introduced medical implement is directly pushed out of the distal end of the tube section into the body cavity. Unless, therefore, the distal end of the tube section is brought as close as possible to the prescribed location within the body cavity to decrease the extent to which an introduced medical implement is pushed out of the tube section, the medical instrument can not be operated freely. Consequently, the prior art types of endoscope have the drawback that they are only applicable to such coeliac section as has a larger width than a sum of the diameter of the tube section and the rate at which the tube section is flexed.

SUMMARY OF THE INVENTION

It is accordingly the object of this invention to provide an endoscope which enables a medical implement pushed out of the distal end of the tube section to be easily and reliably located at the prescribed coeliac position independently of the width of the body cavity, provided said width admits of the easy introduction of the tube section.

According to an aspect of this invention, there is provided an endoscope having a control section and a tube section whose proximal end is connected to the control section and which is provided inside with a medical implement-introducing channel extending from the proximal to the distal end, wherein a guide tube whose end portion corresponding to the distal end portion of the tube section is made flexible and is loaded inside with a medical implement, said end portion of the guide tube being adapted for withdrawal from and introduction into the distal end of the tube section, and a wire received in the tube section and connected at one end to the distal end of the guide tube causes, when pulled toward the control section, that portion of the guide tube which is pushed out of the distal end of the tube section to be easily flexed.

DETAILED DESCRIPTION OF THE PREFERRED EMBODIMENTS

Figure 1:
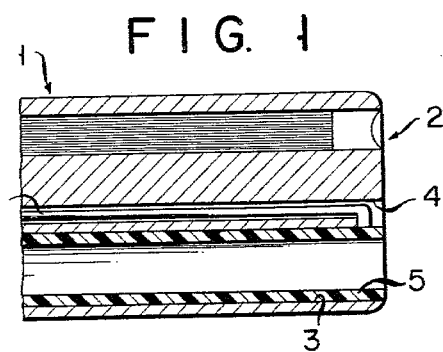
FIG. 1 is a longitudinal sectional view of a tube section of an embodiment of an endoscope according to this invention.
Figure 2:
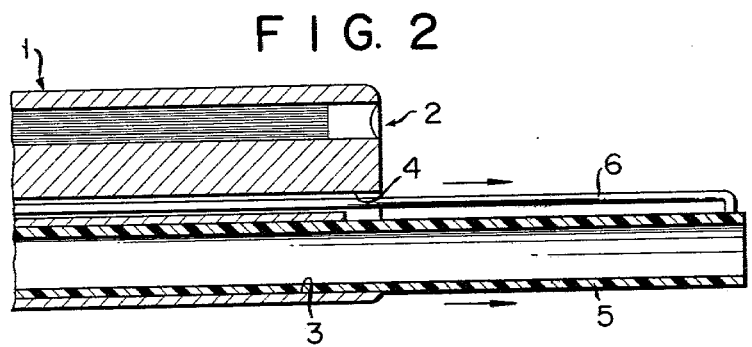
FIG. 2 is a longitudinal sectional view of the tube section of FIG. 1, when both a guide tube and a wire are drawn out of the tube section.
Figure 3:
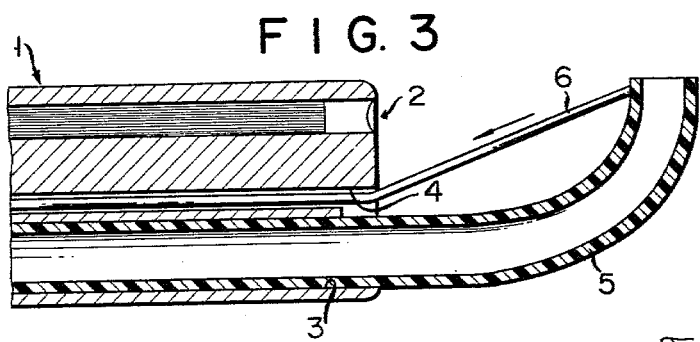
FIG. 3 is a longitudinal sectional view of the tube section of FIG. 1, when the drawn out end portion of the guide tube is flexed by the wire.

Referring to FIGS. 1 to 3, a tube section of an endoscope denoted generally by referential numeral 1 contains an observation optical system 2, illumination optical system (not shown), a first channel 3 and a second channel 4 having a smaller diameter than the first channel 13. The first and second channels 3, 4 are open at the tip end of the distal end portion of the tube section 1. A cylindrical guide tube 5 is longitudinally movably inserted through the first channel 3. A wire 6 is inserted into the second channel 4. The guide tube 5 is prepared from, for example, plastic material and is made flexible along the entire length or at least at the distal end portion. One end of the wire 6 is fixed to the distal end of the guide tube 5, and the other end extends to a control section (not shown) provided at the proximal end of the tube section 1.

There will now be described the operation of an endoscope according to one embodiment of this invention constructed as mentioned above. When the guide tube 5 and wire 6 are made to move forward from the control section, both guide tube 5 and wire 6 are jointly pushed out of the distal end of the tube section 1, as shown in FIG. 2. When the guide tube 5 is pushed out of the distal end of the tube section 1 for the prescribed length and the wire 6 is pulled toward the control section, the guide tube 5 having at least its distal end portion made flexible can be easily bent, as shown in FIG. 3, only with a slight force.

With the known endoscope wherein the distal end of a medical implement is flexed by a control attachment, the medical implement undesirably tends to be shaken or bent due to the absence of a holding member at the distal end, presenting difficulties in being securely set in the prescribed position.

Figure 4:
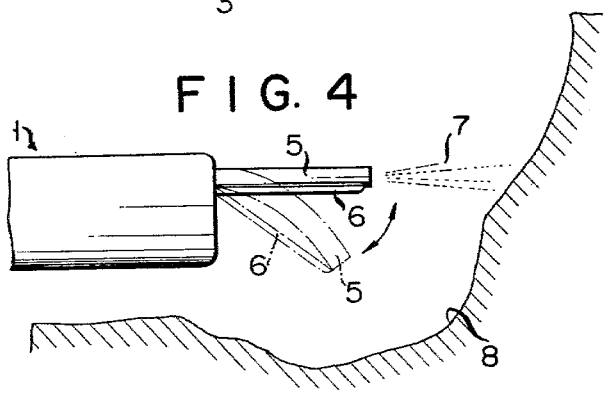
FIGS. 4 to 6 show the various applications of the endoscope of FIG. 1 to the body cavity.
Figure 5:
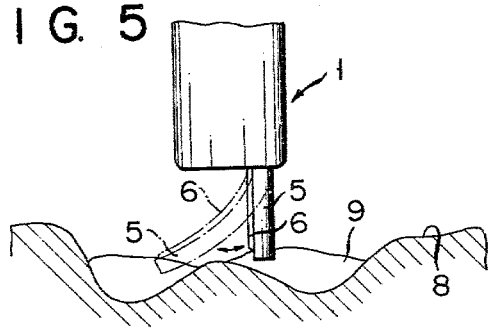
Figure 6:
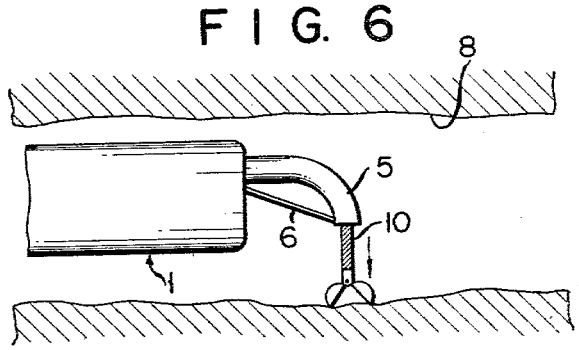

In contrast, the distal end of portion of the guide tube 5 is directly pulled by the wire 6 to be flexed. Therefore, the guide tube 4 is neither unduly shaken nor bent regardless of the extent to which the guide tube 5 is pushed out of the tube section 1. The pulling force of the wire 6 is unfailingly transmitted to the distal end of the guide tube 5, causing the guide tube 5 to be flexed exactly to the desired extent. Further, the guide tube 5 can be flexed with a very much reduced radius of curvature, enabling the present endoscope to be applied without any difficulty even in a narrow body cavity.

Where the medical implement is not inserted into the guide tube 5 (that is, the guide tube 5 is empty), washing liquid is forced, as shown in FIG. 4, into the guide tube 5 so as to be sprayed from the distal end thereof, thereby washing the interior of the body cavity 8. Further, as shown in FIG. 5, water or viscous fluid 9 held in the body cavity 8 can be sucked up through the distal end of the guide tube 5. Where forceps 10 are inserted into the guide tube 5 as illustrated in FIG. 6, a sample of a tissue lying in the body cavity 8 can be picked up. Where any other medical implement is inserted into the guide tube 5, the corresponding treatment can be effected. As mentioned above, the guide tube 5 not only guides a medical implement to the prescribed location of the body cavity 8 but also can be used as a catheter. Once the guide tube 5 is bent toward the prescribed location in the body cavity 8, the medical implement can carry out various types of work while kept in this state. Since it it unnecessary to adjust the bending direction and the degree of bending of the guide tube 5 for each type of work undertaken by the medical implement, a medical treatment can be quickly executed.

When the distal end portion of the guide tube 5 is made softer toward the tip, the guide tube 5 can be more effectively flexed. The embodiments of FIGS. 7 to 9 are intended to promote the flexure of the guide tube 5.

Figure 7:
FIG. 7 is a longitudinal sectional view of another embodiment of a guide tube used for an endoscope of this invention.

Referring to FIG. 7, a guide tube 5, itself is prepared from plastic material. However, the distal end portion 5a in particular is formed of plastics material foamed at a progressively higher rate toward the tip.

Figure 8:
FIG. 8 is a longitudinal sectional view of still another embodiment of a guide tube used for an endoscope of this invention.

Referring to FIG. 8, a guide tube 5, itself is similarly formed of plastic material. However, the wall of said guide tube 5 is made thinner toward the distal end portion 5b.

Figure 9:
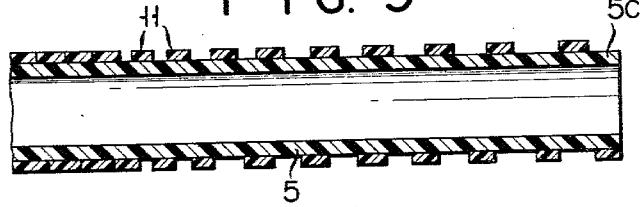
FIG. 9 shows a longitudinal sectional view of further embodiment of a guide tube used for an endoscope of this invention.

Referring to FIG. 9, the guide tube 5 is constructed by winding a coil 11 of plastic or metal material about the guide tube 5 of FIG. 1 at a progressively larger pitch toward the distal end portion 5c.

Figure 10:
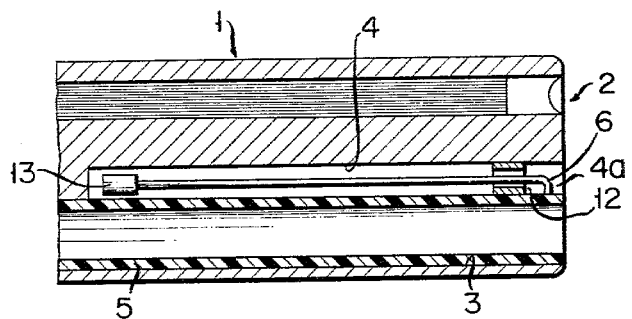
FIG. 10 is a longitudinal sectional view of a tube section of another embodiment of an endoscope according to this invention.

Referring to the embodiment of FIG. 10, a channel 4 does not extend along the entire length of a tube section 1. A tubular engagement member or sleeve 12 is received in a part 4a axially extending through the distal end portion of the tube section 1 and opened at the tip of said distal end portion. A wire 6, one end of which is fixed to the distal end of a guide tube 5 passes through the hole of the sleeve 12, that is, through the channel 4. A stop 13 having a larger diameter than the hole of the sleeve 12 is attached to the other end of the wire 6. The other part of the embodiment of FIG. 10 has the same construction as that of the endoscope of FIG. 1, description thereof being omitted. Obviously, a guide tube 5 may be replaced by any of the guide tube 5 shown in FIGS. 7 to 9.

Figure 11:
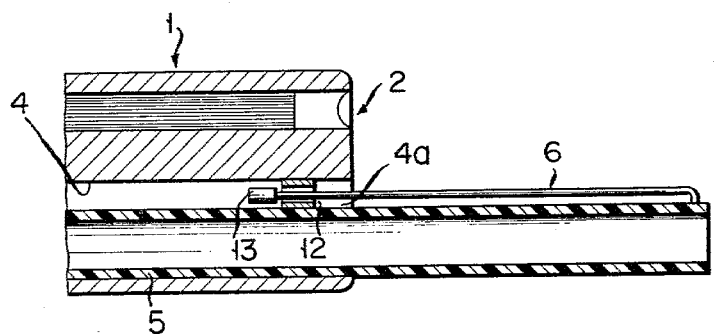
FIG. 11 is a longitudinal sectional view of the tube section of FIG. 10, when both a guide tube and a wire are drawn out of the tube section.
Figure 12:
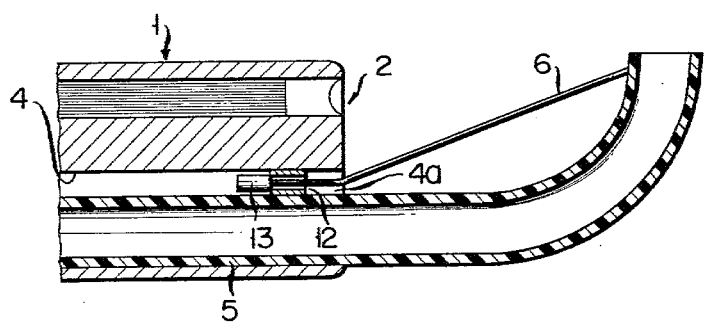
FIG. 12 shows a longitudinal sectional view of the tube section of FIG. 10, when the drawn out end portion of the guide tube is flexed by the wire.

There will now be described the operation of the embodiment of FIG. 10. As shown in FIG. 11, the distal end portion of the guide tube 5 is pushed straight forward out of the distal end of the tube section 1 until the stop 13 abuts against the rear end of the sleeve 12. Where the guide tube 5 is forcefully pushed forward even after the stop 13 touches the rear end of the sleeve 12, the wire 6 pulls back that portion of the guide tube 5 which has been pushed out of the distal end portion of the tube section 1. As a result, the guide tube 5 is flexed as illustrated in FIG. 12. As the guide tube 5 projects more from the distal end of the tube section 1, the curvature of radius of that portion of the guide tube 5 which projects from the distal end of the tube section 1 becomes smaller. Thus, said curvature of radius is determined by the length of said projecting portion of the guide tube 5. The advantage of the last embodiment of FIGS. 10 to 12 is that the guide tube 5 can be flexed simply by being pushed out of the distal end of the tube section 1 to a desired extent, instead of pulling the wire 6 at the control section.

What is claimed is:

1. An endoscope comprising:
a control section;
a tube section having two ends, one end thereof being connected to said control section;
a channel extending through said tube section;
a flexible guide tube having two ends and an outer surface, for surrounding a medical instrument and reciprocatingly movable in said channel so as to allow one of said two ends of said guide tube to project from the other end of said tube section;
an engaging member formed on an inner wall of the tube section;
a wire extending in said tube section along said outer surface of said guide tube, said wire having two ends, one end thereof being inserted into the channel and the other end being fastened to said one of said two ends of said guide tube;
a stop provided in said tube section and connected to said one end of said wire, said stop being movable axially along said tube section together with said guide tube until said stop abuts against said engaging member and allowing said wire to gradually bend that portion of said guide tube which projects from said other end of said tube section, as said one of said two ends of said guide tube projects therefrom after said stop abuts against said engaging member.

2. An endoscope according to claim 1, wherein said portion of the guide tube is progressively more flexible toward a tip thereof.

3. An endoscope according to claim 2, wherein said portion of the guide tube is prepared from plastic material foamed at a progressively higher rate toward the tip.

4. An endoscope according to claim 2, wherein said portion of the guide tube is progressively more reduced in wall thickness toward the tip.

5. An endoscope according to claim 2, wherein the guide tube is wound with a flexible coil whose turns are arranged at a progressively greater pitch toward the tip.

6. An endoscope according to claim 1, wherein the engaging member is a sleeve through which the wire passes, and which is made engageable with the stop.

* * * * *